United States Patent [19]

Cook et al.

[11] 4,148,993
[45] Apr. 10, 1979

[54] PROCESS TO PRODUCE 1-METHYL ISOGUANOSINE

[75] Inventors: Alan F. Cook, Cedar Grove, N.J.; Ronald J. Quinn, Cromer, Australia

[73] Assignee: Hoffmann-La Roche Inc., Nutley, N.J.

[21] Appl. No.: 876,768

[22] Filed: Feb. 10, 1978

[51] Int. Cl.² .................... C07H 17/00; A61K 31/70
[52] U.S. Cl. ........................... 536/24; 536/23; 536/26; 424/180
[58] Field of Search ................... 536/24, 23, 26

[56] References Cited

U.S. PATENT DOCUMENTS

| 3,332,935 | 7/1967 | Yamagaki et al. | 536/24 |
| 3,450,693 | 6/1969 | Suzuki et al. | 536/26 |

FOREIGN PATENT DOCUMENTS

| 42-10517 | 7/1967 | Japan | 536/24 |
| 44-5225 | 4/1969 | Japan | 536/24 |
| 45-16713 | 10/1970 | Japan | 536/24 |

*Primary Examiner*—Johnnie R. Brown
*Assistant Examiner*—Blondel Hazel
*Attorney, Agent, or Firm*—Jon S. Saxe; Bernard S. Leon; Frank P. Hoffman

[57] ABSTRACT

A process to produce 1-methyl isoquanosine, a compound of the formula

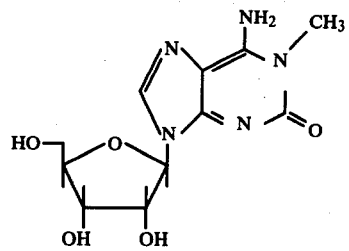

is disclosed. Also disclosed is a novel intermediate in said process. The 1-methyl isoguanosine has been found to have pharmacological activity, e.g. anti-inflammatory activity and muscle relaxant activity.

2 Claims, No Drawings

PROCESS TO PRODUCE 1-METHYL ISOGUANOSINE

DESCRIPTION OF THE INVENTION

There is disclosed a process to produce 1-methyl isoguanosine, a compound of the formula

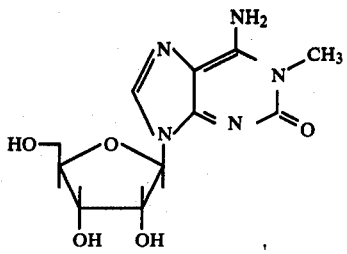

The process comprises the first step reaction of a 5-amino-4-cyano imidazole* of the formula

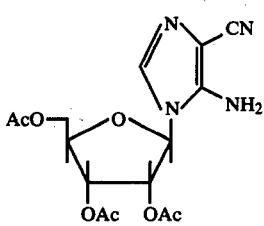

with methyl isocyanate ($CH_3NCO$) in the presence of a powerful aprotic solvent such as dimethylformamide, dimethylsulfoxide or hexamethylphosphoramide. The reaction is carried out at a temperature range of from about room temperature to 150° C. with about 100° C. as preferred.

*U.S. Pat. No. 3,450,693 to Suzuki et al. issued June 17, 1969

The above reaction produces a novel intermediate of the formula

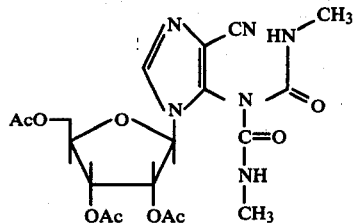

This intermediate is thereafter reacted with a weak base, such as, ammonium hydroxide with or without a $C_1$ to $C_4$ alcohol, anhydrous ammonia together with a $C_1$ to $C_4$ alcohol, or an alkali metal hydroxide, such as, sodium or potassium hydroxide. This cyclization reaction is carried out at from about 0° C. to 100° C. with about room temperature as preferred.

The final product is novel and the subject of a further patent application. The compound exhibits pharmacological activity in the area of muscle relaxant activity. The muscle relaxant effect ($ED_{50}$) in mice has been calculated to be 3.1 mg/kg (ip) and 12 mg/kg (po). The lethal dose in mice ($LD_{50}$) has been calculated to be greater than 2000 mg/kg (po).

Other activities exhibited by the compound include anti-allergic, anti-inflammatory, central nervous system and hypotensive activity.

A suitable pharmaceutical disage form utilizes about 1 to 100 mg of 1-methyl isoguanosine. The oral dosage form may be utilized in various animal species in an amount of about 0.1 to 25 mg/kg daily while for parenteral use the dose is in the range of from about 0.01 to 10 mg/kg daily. It should be understood, however, that the dosage administration to a particular patient is variable, depending upon the clinician's judgment using as the criteria the condition and size of the patient and the patients response thereto.

The compound may be incorporated in an oral dosage form such as tablets, capsules or elixirs or in an injectable form in a sterile aqueous vehicle prepared according to conventional pharmaceutical methods.

The nature and objects of the present invention although not limited thereto can be more fully understood by making reference to the following examples.

EXAMPLE 1

1-Methyl Isoguanosine

A solution of 5-amino-4-cyano-1-(2',3',5'-tri-O-acetyl-β-D-ribofuranosyl)imidazole 25.4 g, 69.3 mmole) and methyl isocyanate (40.9 ml, 693 mmole-Aldrich) in DMF (250 ml, dried over 4 A molecular sieves) was heated with stirring at 100° (oil bath temp). After 6 hr. the reaction was cooled, evaporated to an oil and coevaporation with methanol (250 ml) removed small amounts of residual DMF to give an amber foam. This material was dissolved in methanol (250 ml), filtered through celite to remove small amounts of vacuum grease and evaporated to dryness. After evacuation overnight, the foam was dissolved in methanol (150 ml), treated with concentrated ammonium hydroxide (150 ml) at 5° overnight, and crystals were slowly deposited. These crystals were collected, washed with methanol and recrystallized from ethanol/water, 1:1. Several recrystallizations were necessary to remove minor amounts of an impurity.

MP 265°-266° dec. IR 3400,3355,3190,3110 (NH, OH), 1690 $cm^{-1}$ (C=O), 1645 (C=N). UV ($H_2O$) $\lambda_{max}$ 209 nm ($\epsilon$ 24780), 249 (8300), 293 (11050). UV (0.1 N HCl) $\lambda_{max}$ 211 nm ($\epsilon$ 25750), 236 (5400), 282 (12200). UV (0.15 N $NH_4OH$) $\lambda_{max}$ 210 ($\epsilon$ 21900), 251 (8300), 290 (10900). NMR (DMSO) δ8.12, s, 2 ($NH_2$), 7.90, s, 1 (=CH), 5.65, m, 2 ($C_1'$-H, OH), 5.31, d, 1, J=6 Hz (OH), 5.06, d, 1, J=5 Hz (OH); 4.54, m, 1 (CH), 4.08, m, 1 (CH), 3.92, m, 1 (CH), 3.56, m, 2 ($CH_2$), 3.34, s, 3 ($CH_3$). $[\alpha]_D$—52.9° (1% in $H_2O$).

Calcd for $C_{11}H_{15}N_5O_5$: C, 44.44, H, 5.09, N, 23.56. Found: C, 44.25, H, 5.14, N, 23.68.

EXAMPLE 2

4-Cyano-5-bis-Methylcarbamoyl-Amino-1-(2',3',5'-tri-O-Acetyl-β-D-Ribofuranosyl)Imidazole A solution of 5-amino-4-cyano-1-(2',3',5'-tri-O-acetyl-β-D-ribofuranosyl)imidazole (5 g) in DMF (50 ml, dried over 4 A molecular sieve) was treated with methyl isocyanate (8.05 ml)w/stirring at 100° (bath temp.) for 23 hr, using a reflux condenser. The solution was evaporated to dryness, coevaporated with methanol (2×50 ml) and evacuated overnight to give a froth. A portion (4.76 g) of this material was dissolved in ethyl acetate/chloroform (3:1, 48 ml) and applied to a silica gel column (4.4×98 cm) which had been packed in the same solvent. The column was eluted with ethyl acetate/chloroform (3:1) and fractions of 20 ml were collected. Fractions 122-160 were combined and evaporated to a white foam. Since thin layer chromatography on silica gel (chloroform/methanol 50:1) indicated that this material was impure, the foam was dissolved in chloroform/methanol (50:1, 10 ml) and applied to another silica column (4×65 ml) which had been packed in, and was eluted with chloroform/methanol (50:1). Fractions 100–140 (20 ml each) were evaporated to dryness to give 4-cyano-5-bis-methylcarbamoyl-amino-1-(2′,3′,5′-tri-O-acetyl-β-D-ribofuranosyl) imidazole as a white foam. IR 2245 cm$^{-1}$ (C≡N), 1753 (ester), 1728, 1680 (urea carbonyl). UV sh 227 nm ($\epsilon$ 11,360) in methanol. sh 226 nm ($\epsilon$ 9540) in O.1N HCl. NMR (Me$_2$SO-d$_6$) δ8.33, d, 1 (NHCH$_3$), δ7.65, d, 1 (NHCH$_3$), 5.49 d, 1 (H$_1$′), 5.3, m, 2 (H$_2$′, H$_3$′), 4.29, s, 3 (H$_4$′, 2×H$_5$′), 2.72, d, 3, J=4H$_z$ (NHCH$_3$), 2.63, d, 3, J=4H$_z$ (NHCH$_3$) 2.04, s, 6 (CH$_3$CO), 1.98, s, 3 (CH$_3$CO).

Anal: Calcd for C$_{19}$H$_{24}$N$_6$O$_9$: C 47.49; H, 5.03,; N, 17.49. Found: C, 47.19; H, 5.43; N, 17.70.

EXAMPLE 3

1-Methyl-Isoguanosine from 5-Cyano-4-bis-Methylcarbamoyl-Amino-1-(2′,3′,5′-tri-O-acetyl-β-D-Ribofuranosyl)Imidazole A solution of 5-cyano-4-bis-methylcarbamoyl-amino-1-(2′,3′,5′-tri-O-acetyl-β-D-ribofuranosyl)imidazole (480 mg) in methanol (5 ml) and concentrated ammonium hydroxide (5 ml) was stored at 5° C. for 18 hr. The product was evaporated to dryness and recrystallized from ethanol/water to give 1-methyl isoguanosine MP 267°–268° dec.

What is claimed:

1. A compound of the formula

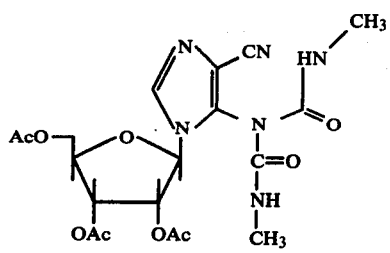

2. A process to produce a compound of the formula

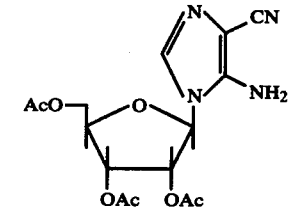

which comprises:

(A) reacting a compound of the formula

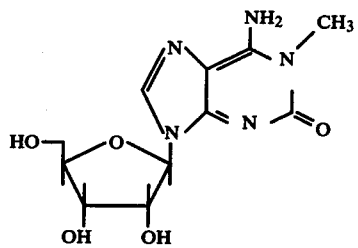

with methyl isocyanate in the presence of a powerful aprotic solvent, and (B) reacting the open product of (A) with ammonium hydroxide to cyclize the open product of (A).

* * * * *